United States Patent [19]

Doi

[11] Patent Number: 4,461,283

[45] Date of Patent: Jul. 24, 1984

[54] ENDOSCOPIC LASER COAGULATOR

[75] Inventor: Yuzuru Doi, Niiza, Japan

[73] Assignee: Kabushiki Kaisha Medos Kenkyusho, Japan

[21] Appl. No.: 364,651

[22] Filed: Apr. 2, 1982

[30] Foreign Application Priority Data

Apr. 10, 1981 [JP] Japan .................................. 56-54531

[51] Int. Cl.³ ................................................ A61B 1/06
[52] U.S. Cl. ..................................... 128/7; 128/303.1
[58] Field of Search ............................. 128/303.1, 6, 7

[56] References Cited

U.S. PATENT DOCUMENTS 3,547,125 12/1970 Tagnon ............................ 128/303.1
4,286,585 9/1981 Ogawa .................................... 128/6
4,313,431 2/1982 Frank ...................................... 128/7

Primary Examiner—John D. Yasko
Attorney, Agent, or Firm—Steinberg & Raskin

[57] ABSTRACT

An endoscopic laser coagulator provides laser beam irradiation in an oblique direction relative to the axis of the insertion tube of the endoscope and includes an insertion tube having a leading end adapted to be introduced into the body and an elongate laser beam conducting fibre extending through the insertion tube. The laser beam conducting fibre is bent at a region proximate to the leading end of the insertion tube such that an oblique laser beam irradiation is obtained relative to the axis of the insertion tube.

9 Claims, 5 Drawing Figures

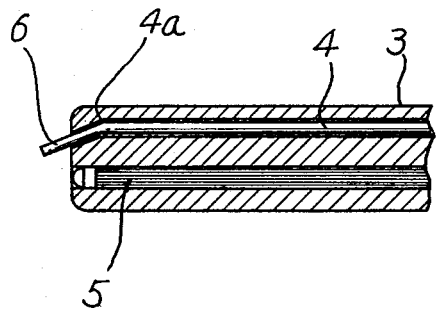
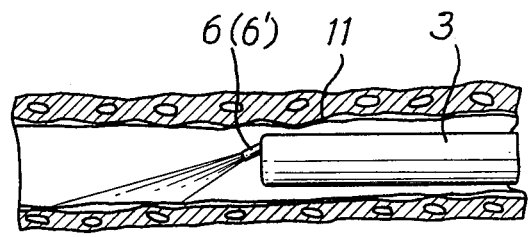
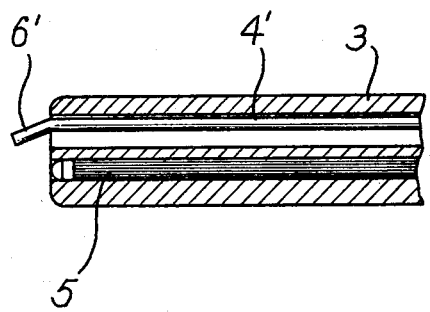
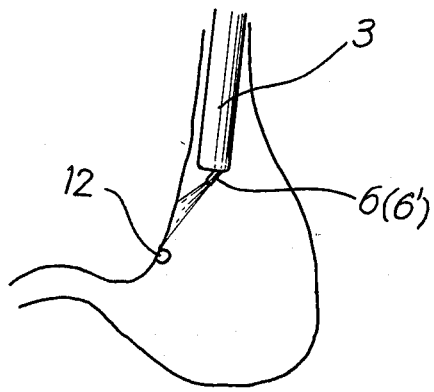
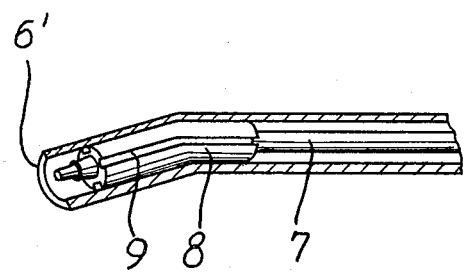

ENDOSCOPIC LASER COAGULATOR

BACKGROUND OF THE INVENTION

The present invention relates generally to endoscopic laser coagulators and, more particularly, to an endoscopic laser coagulator adapted to provide laser beam irradiation in an oblique direction relative to the axis of the insertion tube thereof.

Endoscopes are generally adapted to accomplish one or more tasks. For example, endoscopes are often utilized to observe or photograph particular regions within the body as well as to diagnose and obtain samples of tissue cells. In order to perform such operations, conventional endoscopes usually comprise an insertion tube adapted to be introduced to various organs of the body, such as the stomach, respiratory system or intestine, and in which an optical image transmitting fibre is provided to obtain visual observation of the affected area.

Endoscopic laser coagulators are particularly adapted to therapeutically irradiate a diseased region with a laser beam. For example, such laser beam irradiation may be useful for hemostatic purposes or for the elimination of polyps, such as in the stomach or the like, or of constrictions present in the trachea, bronchus, etc.

However, conventional endoscopic laser coagulators have the drawback that in certain applications it is not possible to achieve effective and appropriate laser beam irradiation of the diseased area. More particularly, when the diseased area is located in body organs presenting a limited or restricted space, it is not possible to bend the forward end region of the flexible insertion tube in order to direct the laser beam irradiation in the desired direction. For example, when the flexible insertion tube is introduced into a segmental bronchus in order to therapeutically treat a diseased area on the wall thereof, little or no clearance will exist between the flexible insertion tube and the bronchus wall in order to effect appropriate bending of the insertion tube and, consequently, it has not been possible to use conventional endoscopic laser coagulators to achieve effective and appropriate laser beam irradiation in such applications.

A reduction of the diameter of the flexible insertion tube will not completely resolve the problem discussed above due to certain inherent functional limitations. Thus, when the region to be irradiated is situated on the wall of an organ having a reduced curvature such, for example, as the stomach, the flexible insertion tube of the endoscope inevitably tends to become situated adjacent to the wall of the stomach so that a force which is applied to bend the forward portion of the flexible insertion tube often results in moving the front end region of the flexible insertion tube into contact with the stomach wall thereby rendering the laser beam irradiation of the diseased area impossible.

In an attempt to overcome the problems of therapeutic irradiation by endoscopic laser coagulators as discussed above, and in particular to accomplish laser irradiation of the wall of the bronchus, endoscopic laser coagulators have been utilized in which the desired therapeutic irradiation is effected utilizing the peripheral energy of the laser beam emitted from the laser beam conducting fibre rather than the central portion of the emitted laser beam. Thus, it is understood that in conventional endoscopic laser coagulators, a laser beam is emitted from the forward or leading end of the flexible insertion tube and that such laser beam will normally diverge defining an angle of irradiation of about 10°. As noted above, it has been proposed to utilize the peripheral regions of the diverging irradiation beam to therapeutically treat diseased regions which are situated in areas where it is not possible to bend the flexible tube into direct confronting relationship.

However, this technique has not proven to be entirely satisfactory since its use has often resulted in serious damage to healthy tissue proximate to the diseased region and which is located in the central or normal region of the beam of laser irradiation. Therefore, this technique has proven to be too dangerous to be employed in practice.

Another possible solution to the problems discussed above has been suggested wherein the flexible insertion tube of the endoscope is equipped to provide a lateral irradiation field rather than a view of the field parallel to the axis of the elongate flexible tube. Use of such lateral viewing type flexible insertion tubes, however, will result in the end surface of the laser beam conducting fibre from which the laser beam is emitted to become positioned unduly close to or even in contact with the wall of the organ to be treated. As a consequence, the energy of the laser beam irradiation may become so intense as to actually burn a hole in the organ wall. In addition to the obvious serious implications of such action, the destroyed tissue will tend to cling to the end surface of the laser beam conducting fibre resulting in the destruction thereof with continued use.

SUMMARY OF THE INVENTION

Accordingly, one object of the present invention is to provide a new and improved endoscopic laser coagulator which eliminates the drawbacks of conventional apparatus described above.

Thus, it is an object of the present invention to provide a new and improved endoscopic laser coagulator which will provide a reliable and effective laser beam irradiation of a diseased tissue area even in narrow or constricted body regions, such as the segmental bronchus or stomach wall without the risk of damaging adjacent healthy tissue areas or burning a hole in the diseased tissue region and while avoiding the possibility of the destruction of the end surface of the laser beam conducting fibre.

Briefly, in accordance with the present invention, these and other objects are attained by providing an endoscopic laser coagulator including an elongate insertion tube adapted to be introduced into the body and elongate laser beam conducting fibre means extending through the insertion tube and wherein the laser beam conducting fibre means is bent at a region proximate to the leading end of the insertion tube such that an oblique laser beam irradiation is obtained relative to the axis of the insertion tube.

DESCRIPTION OF THE DRAWINGS

A more complete appreciation of the present invention and many of the attendant advantages thereof will be readily understood by reference to the following detailed description when considered in connection with the accompanying drawings in which:

FIG. 1 is an axial section view illustrating the forward or leading end region of one embodiment of an endoscopic laser coagulator according to the present invention;

FIG. 2 is a view similar to FIG. 1 illustrating another embodiment of an endoscopic laser coagulator according to the present invention;

FIG. 3 is a partial section view on an enlarged scale illustrating a forward end region of laser beam conducting fibre means used in the embodiment of the invention illustrated in FIG. 2;

FIG. 4 is a schematic illustration of an endoscopic laser coagulator according to the present invention inserted into one of the bronchi lobares and irradiating a diseased region of the wall thereof; and FIG. 5 is similar to FIG. 4 and illustrating the irradiation of the stomach wall utilizing an endoscopic laser coagulator according to the present invention.

DESCRIPTION OF THE PREFERRED EMBODIMENTS

Referring now to the drawings wherein like reference characters designate identical or corresponding parts throughout the several views, and more particularly to FIG. 1, the forward or leading end region of an endoscopic laser coagulator according to the present invention is illustrated. The coagulator comprises an elongate flexible insertion tube 3 in which an elongated guide channel 4 is formed which extends substantially parallel to the axis of the flexible tube 3 and which is adapted to accommodate laser conducting fibre means 6. According to the embodiment of the invention illustrated in FIG. 1, the guide channel 4 has a forwardmost portion 4a which extends at an angle, i.e., is bent, with respect to the major length of the guide channel. The portion 4a of the guide channel 4 thus extends obliquely with respect to the axis of the flexible insertion tube 3 and the juncture of the guide channel portion 4a may be situated, for example, about 2 mm rearwardly of the front or leading end of the flexible tube 3.

The endoscopic laser coagulator is further provided with image transmitting fibre means 5 extending through the flexible insertion tube 3 as seen in FIG. 1. The image transmitting fibre means 5 provides a visual field of observation so that the operator may observe the diseased tissue area. The guide channel portion 4a is formed so that its axis will substantially intersect the visual field of the image transmitting fibre means 5.

It will be understood that when the laser beam conducting fibre means 6 is received within the guide channel 4, the fibre means will be bent at the region of the juncture of the guide channel portion 4a and the major portion of the guide channel 4 so that a forward substantially rectilinear length portion of the fibre means 6 will extend obliquely with respect to the axis of the insertion tube. As seen in FIG. 1, the end of the laser beam conducting fibre means 6 extends beyond the end surface of the flexible tube 3.

Referring to FIG. 2, another embodiment of the present invention is illustrated. According to this embodiment, the laser beam conducting fibre means 6' has a forward end region which is prebent at a predetermined angle with respect to the major portion of the fibre means so as to extend obliquely with respect thereto. It is noted that the guide channel 4' in the embodiment illustrated in FIG. 2 has a diameter which is larger than the diameter of the laser beam conducting fibre means 6' so that the fibre means 6' including the prebent forward end portion thereof can be inserted and guided through the guide channel 4' without difficulty. The fibre means 6' is secured within the guide channel 4' with the axis of the obliquely extending forward length portion thereof substantially intersecting the visual field provided by the image transmitting fibre means 5.

The embodiment of FIG. 2 is particularly advantageous in that the laser conducting fibre means 6' has sufficient rigidity such that the position thereof with respect to the flexible tube 3 can be manipulated by suitable means provided at the rearward end of the endoscope. Thus, the laser beam conducting fibre means 6' can be freely rotatable relative to the flexible tube 3 or may be advanced or retracted within the guide channel 4' to provide the capability of accurately directing the irradiation from the laser beam onto a desired area.

Turning now to FIG. 3, a favorable construction of the forward end region of laser beam conducting fibre means 6' used in the embodiment of the invention illustrated in FIG. 2 is illustrated. The fibre means 6' includes an outer sheath through which a fibre member 7 which guides the laser beam passes. A centering holding member 8 is provided which in the illustrated embodiment comprises a body member formed of a pair of substantially cylindrical body portions extending obliquely with respect to each other and through which a central bore is formed defined by a pair of bore lengths which extend obliquely with respect to each other in a corresponding manner. It will be understood that the angle at which the bore lengths extend relative to each other corresponds to the angle at which the laser beam conducting fibre means 6' is prebent. Thus, the centering holder member 8 may comprise a hollow pipe formed of synthetic resin, such as a hexafloride. Moreover, a suitable number of ventilating grooves 9 are formed in the peripheral surface of the holding member 8 axially extending between the end surfaces thereof. Gases, such as air, may be fed through the ventilating grooves 9 in order to prevent debris or condensate from clinging to the front end surface of the fibre means 6' during laser beam irradiation of the tissue.

The irradiation of a diseased area within one of the bronchi lobares or segmental bronchi by an endoscopic laser coagulator according to the present invention is illustrated in FIG. 4. Thus, the flexible insertion tube 3 is inserted within the bronchus 11 and laser beam irradiation applied to the effected area by means of the laser beam conducting fibre means 6, 6'.

FIG. 5 similarly illustrates the laser beam irradiation of a diseased area on a stomach wall 12 by means of an endoscopic laser coagulator according to the present invention including a flexible insertion tube 3 and laser beam conducting fibre means 6, 6'.

It will be understood that the endoscopic laser coagulator will normally include means for providing and directing a guide light beam in an axial coinciding manner with the laser beam so that the precise spot on which the laser beam will be directed and the extent of coagulation can be determined prior to the actual irradiation being accomplished in order to assure a reliable and safe operation.

Thus, the endoscopic laser coagulator will generally include means for providing and directing a guide beam as well as an image transmitting fibre means having a relatively wide visual field. Since the laser beam conducting fibre means 6' may be advanced, retracted or rotated relative to the flexible insertion tube 3 after the same has been located adjacent to a diseased tissue area to be irradiated, the diseased area may be precisely irradiated by a laser beam having a high degree of maneuverability.

The endoscopic laser coagulator of the present invention enables the irradiation of a given area by a laser beam to be reliably carried out in an easy manner even where the diseased area is located in a position wherein such irradiation has been impossible or dangerous utilizing conventional endoscopic laser coagulators. For example, laser coagulation of areas lying on the wall of bronchi lobares wherein the flexible tube cannot be bent or of areas lying on the curved wall of the stomach can be irradiated without the danger that such irradiation will affect the adjacent healthy areas. Moreover, the apparatus of the present invention is simple in construction and can be obtained merely by partially modifying the construction of the forward end regions of the guide channels of conventional endoscopic laser coagulators or by prebending the forward end regions of the laser beam conducting fibre means without modifying the conventional guide channels in the flexible tubes of conventional endoscopes thereby rendering the manufacturing costs advantageously low. It will also be understood that the apparatus according to the present invention may be used as a laser knife with a high degree of safety and reliability.

Obviously, numerous modifications and variations of the present invention are possible in the light of the above teachings. It is therefore to be understood that within the scope of the claims appended hereto, the invention may be practiced otherwise than as specifically disclosed herein.

What is claimed is:

1. An endoscopic laser coagulator comprising:
   an elongate insertion tube having a leading end adapted to be introduced into a body and elongate laser beam conducting fibre means extending through said insertion tube,
   said laser beam conducting fibre means including a forward, substantially rectilinear length portion proximate to said leading end of said insertion tube,
   said length portion having a longitudinal axis which extends obliquely with respect to the axis of said insertion tube,
   wherein a major length of said laser beam conducting fibre means extends through said insertion tube in a direction substantially parallel to the axis of said insertion tube, and
   wherein said laser beam conducting fibre means are permanently bent at a region proximate to said leading end of said insertion tube to define said forward length portion thereof,
   such that an oblique laser beam irradiation is obtained relative to the axis of said insertion tube.

2. An endoscopic laser coagulator comprising:
   an elongate insertion tube having a leading end adapted to be introduced into a body,
   elongate laser beam conducting fibre means extending through said tube, and
   an elongate guide channel formed in said insertion tube and adapted to receive said elongate laser beam conducting fibre means,
   wherein said guide channel is angled at a region proximate to said leading end of said insertion tube so as to extend obliquely with respect to the axis of said insertion tube,
   whereby said elongate laser beam conducting fibre means received in said guide channel are bent at a corresponding region thereof proximate to said leading end of said insertion tube.

3. The combination of claim 1 wherein an elongate guide channel is formed in said insertion tube adapted to receive said elongate laser beam conducting fibre means, and wherein said guide channel has a diameter which is larger than the diameter of said laser beam conducting fibre means.

4. The combination of claim 3 wherein said laser beam conducting fibre means includes an outer elongate sheath, a fibre member passing through said sheath for guiding a laser beam, and a centering holding member situated within said sheath in a forward region thereof, said centering holding member having a bore formed therethrough through which said fibre member passes, said bore being defined by a pair of bore lengths which extend obliquely with respect to each other such that the portion of said fibre member which passes through said holding member is bent at a predetermined angle.

5. The combination of claim 4 wherein said centering holding member is constituted by a body member having opposite end surfaces, said body member being formed of substantially cylindrical body portions extending obliquely with respect to each other, each of said bore lengths being centrally formed in a respective one of said body portions.

6. The combination of claim 5 wherein said centering holding member is provided with ventilation means constituted by at least one groove formed in the outer surface of said body member and extending between said end surfaces thereof in a direction substantially parallel to the portion of said fibre member which passes through said centering holding member.

7. The combination of claim 3 wherein said laser beam conducting fibre means can be advanced, retracted and rotated within said guide channel to selectively direct the laser beam irradiation.

8. The combination of claim 1 wherein said endoscopic laser coagulator further includes elongate image transmitting fibre means extending through said insertion tube for providing visual observation of a visual field thereof.

9. The combination of claim 8 wherein the axis of said laser beam conducting fibre means forward of said region at which said fibre means is bent intersects said visual field of said image transmitting fibre means.

* * * * *